US00PP08495P

United States Patent [19]

Meilland

[11] Patent Number: Plant 8,495

[45] Date of Patent: Dec. 14, 1993

[54] HYBRID TEA ROSE PLANT NAMED 'MEIMACAR'

[75] Inventor: Alain A. Meilland, Antibes, France

[73] Assignee: The Conard-Pyle Company, West Grove, Pa.

[21] Appl. No.: 983,321

[22] Filed: Nov. 30, 1992

[51] Int. Cl.[5] ..... A01H 5/00

[52] U.S. Cl. ..... Plt./15

[58] Field of Search ..... Plt./24, 15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms attractive fully double yellow blossoms on very long stems. The blossoms are Primrose Yellow and are more or less suffused with pale Aureolin Yellow. The buds are very large. The blossoms are very long lasting when cut and placed in a vase and their cleaning ability is good. The plant exhibits an upright growth habit, vigorous dark green vegetation, and particularly is suited for cut flower production under greenhouse growing conditions. Also, the new variety exhibits excellent disease resistance.

1 Drawing Sheet

SUMMARY OF THE INVENTION

The new variety of Hybrid Tea rose plant was created by artificial pollination wherein two parents were crossed with previously had been studied in the hope that they would contribute the desired characteristics. The female parent (i.e., the seed parent) of the new variety was the Mabella variety (U.S. Plant Pat. No. 3,228) and the male parent (i.e., the pollen parent) was the Meimiza variety (non-patented in the United States). The Mabella variety sometimes is known as the New Day variety. The parentage of the new variety can be summarized as follows:

Mabella × Meimiza.

The seeds resulting from the above pollination were sown and 9 small plants were obtained which were physically and biologically different from each other. Selective study resulted in the identification of a single plant of the new variety.

It was found that the new variety of Hybrid Tea rose plant of the present invention possesses the following combination of characteristics:

(a) forms large yellow buds,
(b) forms in abundance on very long reddish-tinted stems attractive long lasting fully double yellow flowers which are Primrose Yellow and are more or less suffused with Aureolin Yellow,
(c) exhibits an upright growth habit,
(d) exhibits vigorous dark green vegetation,
(e) is particularly suited for cut flower production under greenhouse growing conditions, and
(f) exhibits excellent disease resistance.

The cleaning ability of the blooms after flowering is excellent.

The new variety well meets the needs of the horticultural industry for a number of uses and is particularly well suited for use during the formation of cut flowers.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the Meimacar variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during February while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
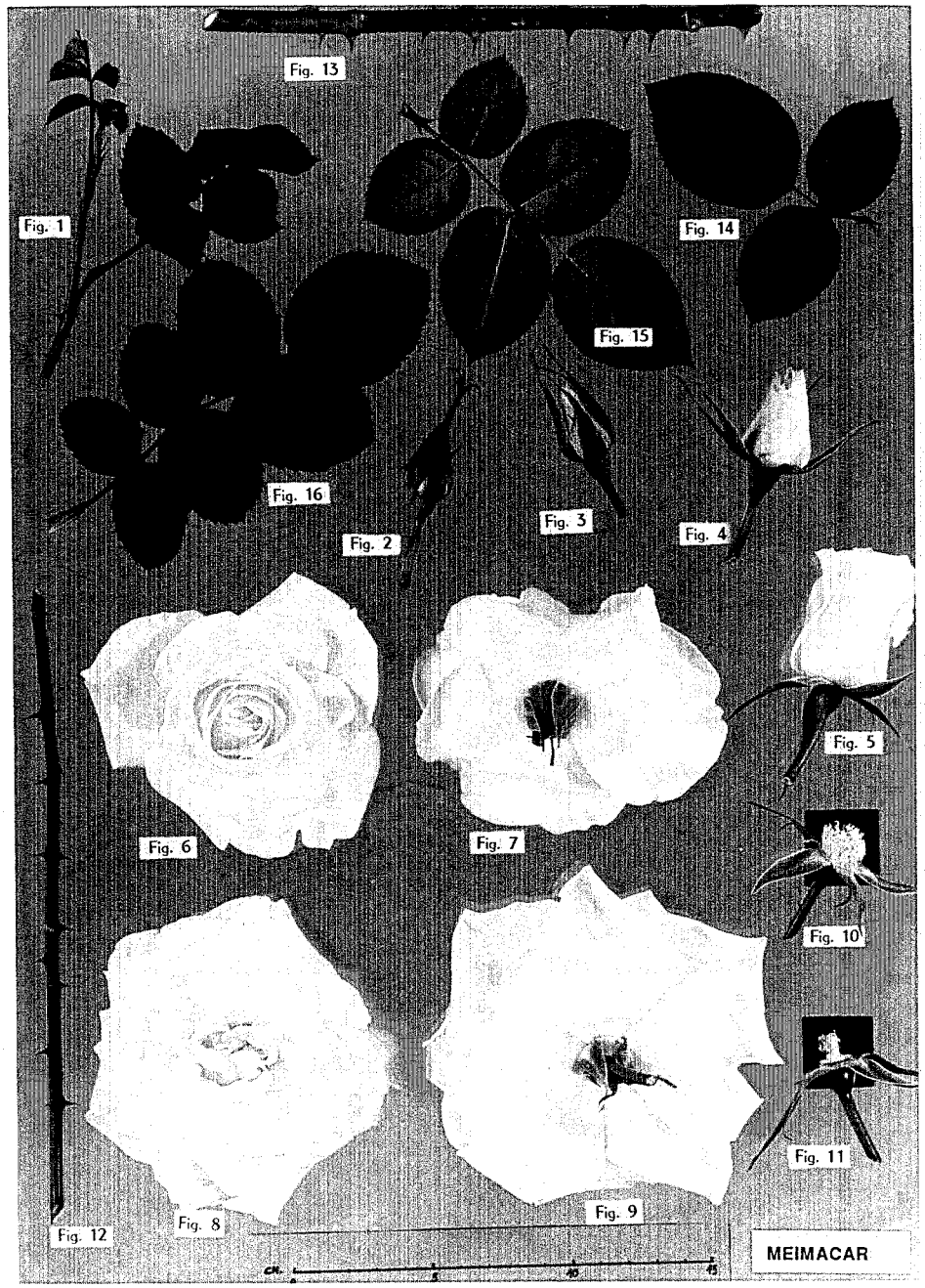
FIG. 1 illustrates a specimen of young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower during the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on the observation of two year old plants made during February while budded on *Rosa indica* understock and growing in greenhouses at Cap d'Antibes, France. The coloration in common terms precedes reference to the chart.

Class: Hybrid Tea.

Plant:

*Height.*—When plants are cut to a height of 85 cm. flowering stems commonly are produced having a length of approximately 50 to 70 cm. When grown in fields at Wasco, Calif., U.S.A., the plants commonly attain a height of approximately 130 cm. at the end of one growing season.

*Habit.*—Upright.

Branches:

*Color.*—Young stems: light green, Green Group 137B, more or less suffused with reddish coloration. Adult wood: dark green, Green Group 137A.

*Thorns.*—Size: large. Quantity: average. Color: pinkish on young stems and reddish-green on mature wood.

Leaves:

*Stipules.*—Adnate, pectinate, wide and linear.

*Petioles.*—Upper surface: striped reddish brown on young foliage and medium green on adult foliage with glandular edges. Under surface: medium green, and bears a few prickles.

*Leaflets.*—Number: 3, 5 (most often), and 7. Shape: elliptic. Serration: single and regular. Texture: consistent. General appearance: dense, dark, bright foliage. Color (young foliage): Upper surface: Bronze Green, Yellow-Green Group 146A, and more or less stained with reddish coloration. Under surface: medium green, Yellow-Green Group 146B, and more or less stained with reddish coloration. Color (adult foliage): Upper surface: dark green, Green Group 137A. Under surface: light green, Green Group 137C.

Inflorescence:

*Number of flowers.*—Usually a single bloom per stem.

*Peduncle.*—Medium green, more or less suffused with reddish coloration, and bears numerous glandular acicules. The length is approximately 9 to 10 cm. on average.

*Sepals.*—Upper surface: tomentose and greenish. Under surface: medium green in coloration, the outer sepals are more or less glandular and have slightly appendiculated edges.

*Buds.*—Shape: conical. Length: approximately 4 cm. on average. Size: large. Color when opening: Upper surface: pale Sulphur Yellow, Yellow Group 6D. Under surface: pale Sulphur Yellow, Yellow Group 6D.

*Flower.*—Shape: cup-like and fully double. Diameter: approximately 14 to 15 cm on average. Color (when opening begins): Upper surface: pale Sulphur Yellow, Yellow Group 6D, more or less suffused with pale Aureolin Yellow, Yellow Group 12D. Under surface: pale Sulphur Yellow, Yellow Group 6D, more or less suffused with pale Aureolin Yellow, Yellow Group 12D. Color (when blooming): Upper surface: Primrose Yellow, Yellow Group 4D, more or less suffused with pale Aureolin Yellow, Yellow Group 12D. Under surface: Primrose Yellow, Yellow Group 4D, more or less suffused with pale Aureolin Yellow, Yellow Group 12D. Color (at end of blooming): Upper surface: Primrose Yellow, Yellow Group 4D, more or less suffused with pale Aureolin Yellow, Yellow Group 12D. Under surface: Primrose Yellow, Yellow Group 4D, more or less suffused with pale Aureolin Yellow, Yellow Group 12D. Fragrance: slight. Lasting quality: long lasting when cut and placed in a vase. Petal number: approximately 27 to 30 on average. Texture: consistent. Petal drop: good. Stamen number: approximately 124 on average. Anthers: normal, yellowish in coloration. Filaments: bright yellow in coloration, and very irregular in height. Pistils: approximately 89 on average. Stigmas: greenish-strawlike. Styles: greenish and more or less twisted. Receptacle: medium green at the dehiscence of the anthers, and in longitudinal section it is in the configuration of a wide pitcher.

Development:

*Vegetation.*—Fairly vigorous.

*Blooming.*—Normal.

*Aptitude to be forced.*—Good.

*Resistance to diseases.*—Excellent.

I claim:

1. A new and distinct variety of the Hybrid Tea rose plant characterized by the following combination of characteristics:

(a) forms large yellow buds,
(b) forms in abundance on very long reddish-tinted stems attractive long lasting fully double yellow flowers which are a Primrose Yellow and are more or less suffused with Aureolin Yellow,
(c) exhibits an upright growth habit,
(d) exhibits vigorous dark green vegetation,
(e) is particularly suited for cut flower production under greenhouse growing conditions, and
(f) exhibits excellent disease resistance;

substantially as herein shown and described.

* * * * *

MEIMACAR